(12) United States Patent
Saito et al.

(10) Patent No.: US 12,133,757 B2
(45) Date of Patent: Nov. 5, 2024

(54) RADIATION IMAGING SYSTEM, RADIATION IMAGING METHOD, AND RECORDING MEDIUM

(71) Applicant: Konica Minolta, Inc., Tokyo (JP)

(72) Inventors: Takeshi Saito, Hachioji (JP); Nobuyuki Miyake, Yokohama (JP); Tomonori Komasaka, Hino (JP); Kosuke Fukazu, Hino (JP)

(73) Assignee: Konica Minolta, Inc., Tokyo (JP)

( * ) Notice: Subject to any disclaimer, the term of this patent is extended or adjusted under 35 U.S.C. 154(b) by 115 days.

(21) Appl. No.: 17/540,822

(22) Filed: Dec. 2, 2021

(65) Prior Publication Data

US 2022/0183650 A1    Jun. 16, 2022

(30) Foreign Application Priority Data

Dec. 14, 2020 (JP) ................ 2020-206390

(51) Int. Cl.
*A61B 6/00* (2024.01)
*A61B 6/04* (2006.01)
*A61B 6/06* (2006.01)
*A61B 6/42* (2024.01)
*A61B 6/46* (2024.01)

(52) U.S. Cl.
CPC ............ *A61B 6/547* (2013.01); *A61B 6/0407* (2013.01); *A61B 6/06* (2013.01); *A61B 6/4208* (2013.01); *A61B 6/4405* (2013.01); *A61B 6/463* (2013.01); *A61B 6/469* (2013.01)

(58) Field of Classification Search
CPC ....... A61B 6/0407; A61B 6/06; A61B 6/4208; A61B 6/4405; A61B 6/463; A61B 6/469; A61B 6/547; A61B 6/4283; A61B 6/4452
See application file for complete search history.

(56) References Cited

U.S. PATENT DOCUMENTS

2012/0230473 A1* 9/2012 Stagnitto ............. A61B 6/4291
378/205

FOREIGN PATENT DOCUMENTS

JP        2014-507247 A    3/2014
JP        2015-023915 A    2/2015

OTHER PUBLICATIONS

Japanese Patent Office, Notice of Reasons for Refusal mailed Mar. 12, 2024, which was issued for related Japanese Patent Application No. 2020-206390, with full English translation, 8 pages.

* cited by examiner

*Primary Examiner* — Dani Fox

(74) *Attorney, Agent, or Firm* — LUCAS & MERCANTI, LLP

(57) ABSTRACT

Disclosed is a radiation imaging system including: a tube that generates a radiation; a radiation detector to generate a radiation image corresponding to the radiation that is received; and a display that starts or ends, at a predetermined timing, displaying of inclination information indicating an inclination of the radiation detector with respect to a horizontal plane or a direction of the tube.

20 Claims, 8 Drawing Sheets

ROLL ANGLE 40°
PITCH ANGLE 0°

ROLL ANGLE 0°
PITCH ANGLE 40°

ROLL ANGLE −40°
PITCH ANGLE 0°

RADIATION IMAGING SYSTEM, RADIATION IMAGING METHOD, AND RECORDING MEDIUM

CROSS-REFERENCE TO RELATED APPLICATIONS

The entire disclosure of Japanese Patent Application No. 2020-206390 filed on Dec. 14, 2020 is incorporated herein by reference in its entirety.

BACKGROUND

Technological Field

The present invention relates to a radiation imaging system, a radiation imaging method, and a recording medium.

Description of the Related Art

A mobile radiation imaging system, called a medical roving vehicle or a medical cast, is sometimes used to perform radiation imaging of an subject, for example, on a bed in a hospital ward.

In the case of imaging on a bed, the imaging surface of the portable (panel-type) radiation detector placed between the subject's back and the bed may not necessarily be parallel or orthogonal (may be inclined) to the horizontal plane.

Even in such a case, it is necessary to adjust the direction of the tube with respect to the radiation detector so that the axis of radiation irradiation is orthogonal to the imaging surface of the radiation detector in order to prevent density differences in the radiation image due to the cutoff of the grid attached to the radiation incidence surface or changes in the positioning of internal structures of the subject that appear on the radiation detector from affecting the diagnosis.

In order to support the user in adjusting the direction of the tube, various technologies have been proposed to display inclination information indicating the inclination of the tube with respect to the radiation detector.

For example, JP 2014-507247 describes a device that includes: a first emitter device that is coupled to a like and can be energized to generate a first magnetic field; a control circuit that energizes the first emitter device; a sensing device with multiple sensor elements located around an image receiver; and a signal generating circuit that generates an output signal indicating a position and a direction of the sensing device relative to the emitter device according to multiple sensor signals from the multiple sensor elements.

JP 2015-023915 describes an X-ray imaging apparatus that includes: an acceleration sensor section that detects the irradiation direction of the X-ray tube and the inclination of the X-ray incidence surface of the X-ray detector based on signals from the acceleration sensor, and a magnetic sensor section that detects the irradiation direction of the X-ray tube and the inclination of the X-ray incidence surface of the X-ray detector based on signals from the magnetic sensor; a judgment means that judges the state of opposing between the X-ray detector and the X-ray tube based on the detection results of the acceleration sensor section or the magnetic sensor section; and a prohibition means that prohibits the use of the detection results of the magnetic sensor section by the judgment means during a specific operation period of the X-ray imaging apparatus.

SUMMARY

In general, radiation imaging using a medical cart involves the following steps in the following order: stop the medical cart at the bedside, adjust the bed angle to place the subject in a sitting position, adjust the approximate position of the tube, remove the radiation detector from the storage area of the medical cart, place the radiation detector between the subject's back and the bed, finely adjust the direction of the tube and the irradiation field, and take the image. In other words, in radiation imaging using a medical cart, the direction of the tube is adjusted roughly and then finely adjusted (adjusted twice). This is done to reduce the amount of time that the hard radiation detector is sandwiched between the subject and the bed as much as possible, thereby reducing the pain that the subject suffers.

However, conventional devices, such as those described in JP 2014-507247 and JP 2015-023915, do not sufficiently consider the timing of displaying inclination information. Therefore, when radiation imaging is performed using these devices in the flow described above, the devices display the inclination information from the stage before the radiation detector is placed between the bed and the subject, which may cause confusion for the user.

The present invention has been made in consideration of the above matters, and the purpose of the present invention is to enable the user to check the inclination information, which indicates the inclination of the radiation detector with respect to the horizontal plane or the direction of tube, at the timing required by the user.

To achieve at least one of the above mentioned objects, according to an aspect of the present invention, a radiation imaging system reflecting one aspect of the present invention is a radiation imaging system including: a tube that generates a radiation; a radiation detector to generate a radiation image corresponding to the radiation that is received; and a display that starts or ends, at a predetermined timing, displaying of inclination information indicating an inclination of the radiation detector with respect to a horizontal plane or a direction of the tube.

To achieve at least one of the abovementioned objects, according to another aspect of the present invention, a radiation imaging system reflecting one aspect of the present invention is a radiation imaging system including: a radiation detector to generate a radiation image corresponding to a radiation that is received; and a hardware processor that calculates inclination information of the radiation detector with respect to a horizontal plane or a direction of a tube which generates the radiation, wherein the hardware processor calculates, as the inclination information, a magnitude of an angle between the horizontal plane and a radiation incidence plane of the radiation detector.

To achieve at least one of the abovementioned objects, according to another aspect of the present invention, a radiation imaging method reflecting one aspect of the present invention is a radiation imaging method including: generating a radiation by a tube: generating, by a radiation detector, a radiation image corresponding to the radiation that is received; and starting or ending, at a predetermined timing, displaying by a display of inclination information indicating an inclination of the radiation detector with respect to a horizontal plane or a direction of the tube.

To achieve at least one of the abovementioned objects, according to another aspect of the present invention, a recording medium reflecting one aspect of the present invention is a non-transitory computer readable recording medium storing a program causing a computer to perform the above radiation imaging method.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF EMBODIMENTS

Embodiments of the present invention will be described below with reference to the drawings. However, the technical scope of the present invention is not limited to the following embodiments and illustrative examples.

<1. Radiation Imaging System>

First, the schematic configuration of a radiation imaging system (hereinafter, referred to as a system 100) according to the embodiment will be described by taking, as an example, a case where a medical cart is configured by the system 100.

Figure 1:
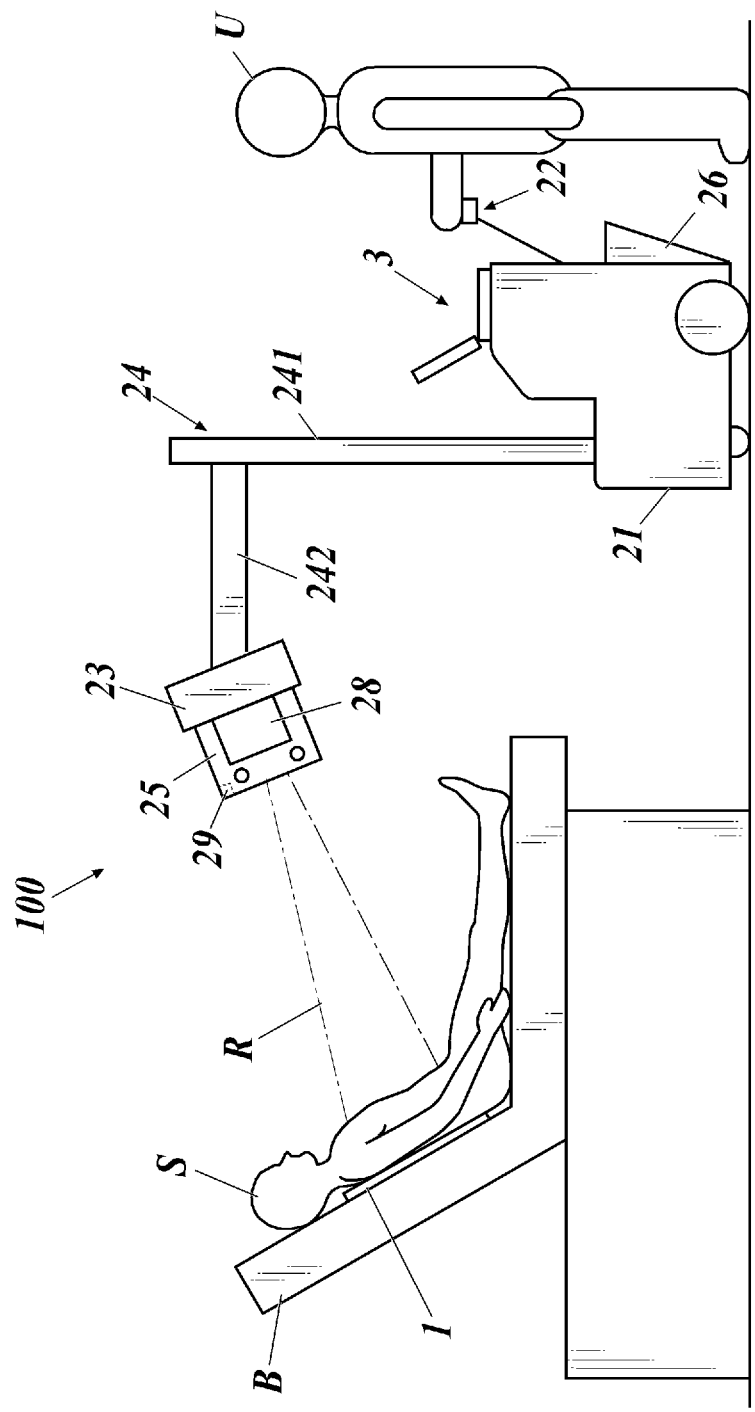
FIG. 1 is a side view of an example of a radiation imaging system according to an embodiment.
Figure 2:
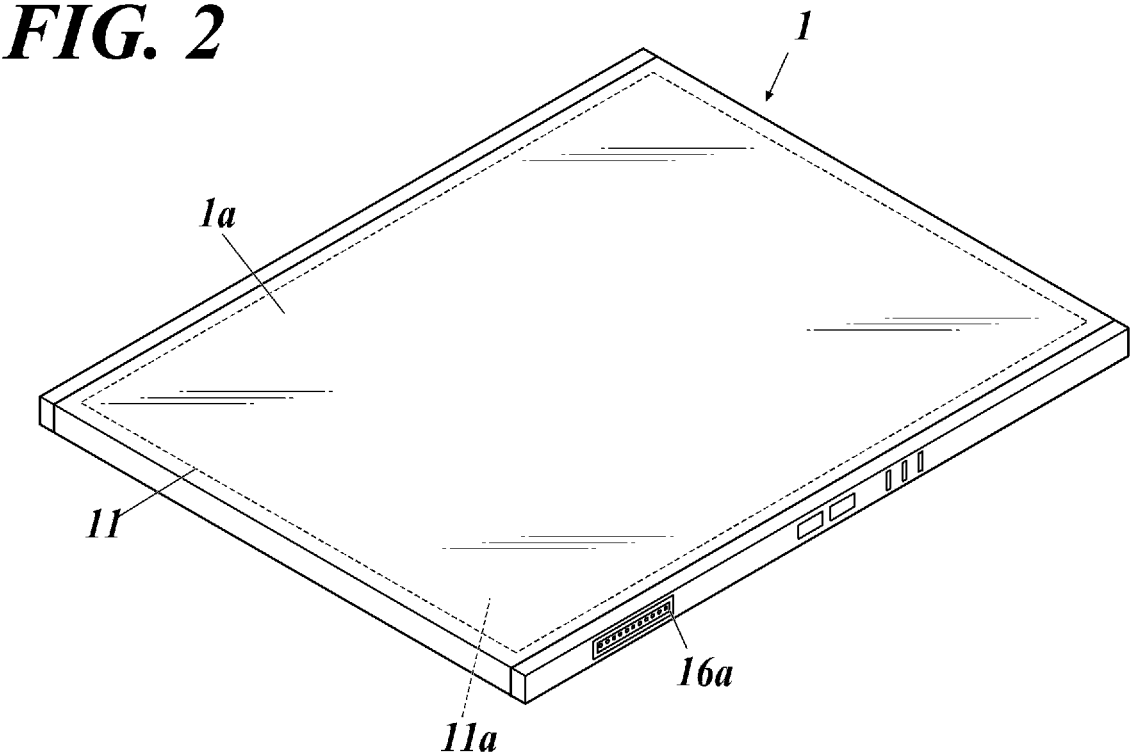
FIG. 2 is an oblique view of the radiation detector shown in the radiation imaging system of FIG. 1.

FIG. 1 is a block diagram of the system 100, and FIG. 2 is a diagram of the radiation detector 1 included in the system 100.

The system 100 includes a radiation detector (hereinafter referred to as a detector 1), a radiation generating device (hereinafter referred to as a generating device 2), and a console 3, as shown for example in FIG. 1.

Each of the devices 1 to 3 can communicate with each other, for example, through a communication network (LAN (Local Area Network), WAN (Wide Area Network), Internet, etc.).

The system 100 may be capable of communicating with the Hospital information System (HIS), Radiology Information System (RIS), Picture Archiving and Communication System (PACS), dynamic state analysis devices, etc., which are not shown in the drawings.

The communication network may be wired or wireless.

[1-1. Radiation Detector]

The detector 1 generates a radiation image according to the radiation R received from the generating device 2.

The detector 1 according tai the embodiment is constructed in the form of a panel, as shown in FIGS. 1 and 2, and can be carried.

For this reason, the detector 1 according to the embodiment can be used not only by loading it on the imaging table, but also by placing the detector t horizontally between the subject S or a lying position on the bed B and the bed B. As shown in FIG. 1, the detector 1 according to the embodiment can also be used by placing the detector 1 in an upright position between the subject S in a sitting position and the backrest of a partially upright bed B or a wheelchair.

The radiation incidence plane 1a (the surface facing the subject S) of the detector 1 loaded on the imaging table is parallel or orthogonal to the horizontal plane. However, in imaging without an imaging table (in a bed B or wheelchair), the radiation incidence plane 1a may not always be parallel or orthogonal to the horizontal plane (may be inclined).

In addition, when the detector 1 is interposed between the subject S and a soft instrument such as a bed B, the detector 1 may move with the movement of the subject S.

The details of this detector 1 will be described later.

[1-2. Radiation Generating Device]

The generating device 2 includes, as shower in FIG. 1, a generating device body 21, an irradiation instruction switch 22, and a tube 23.

The generating device 2 further includes a tube supporter 24, a collimator 25, and a detector storage 26.

The generating device 2 according to the embodiment can be moved by the wheels equipped on the housing.

The details of the generating device body 21 will be described later.

[1-2-1. Irradiation Instruction Switch]

The irradiation instruction switch 22 outputs an operation signal to the generating device body 21 when it is operated (pressed) by the user U.

FIG. 1 shows an example where the irradiation instruction switch 22 is wired to the generating device body 21. However, the irradiation instruction switch 22 and the generating device body 21 may be connected wirelessly.

[1-2-2. Tube]

When the irradiation instruction switch 22 is operated, the tube 23 generates a dose of radiation R (such as X-rays) according to the preset imaging conditions in a manner corresponding to the imaging conditions, and emits the radiation from the radiation port.

[1-2-3. Tube Supporter]

The tube supporter 24 supports the tube 23.

The tube supporter 24 according to the embodiment includes, a first supporter 241 extending to its upper end from the generating device body 21 and a second supporter 242 extending forward from the upper portion of the first supporter 241.

The end of the second supporter 242 supports the tube 23.

The tube supporter 24 has a joint mechanism, not shown in the drawings, to move the tube 23 in the X-axis direction (front-back direction of the generating device 2 (left-right direction of FIG. 1)), in the Y-axis direction orthogonal to the X-axis (width direction of the generating device 2 (direction orthogonal to paper surface of FIG. 1), and in the Z-axis direction orthogonal to the X-axis and Y-axis (vertical direction (up-down direction of FIG. 1)).

In addition, the tube supporter 24 can change the direction of the radiation port by rotating the tube 23 around a rotation axis parallel to the X-, Y-, and Z-axes using a joint mechanism not shown in the drawings.

[1-2-4. Collimator]

The collimator 25 is attached to the radiation port of the tube 23 and narrows the radiation R so that the radiation field of the radiation R emitted from the radiation port becomes a preset rectangular shape.

The collimator 25 includes a lamp button, which is not shown in the drawings.

When the lamp button is operated by the user, visible light is emitted in the area of the irradiation field of radiation R.

[1-2-5. Detector Storage]

The detector storage 26 stores the detector 1 when it is not used.

The detector storage 26 according to the embodiment is provided on a lateral side of the generating device body 21.

The detector storage 26 according to the embodiment can store multiple detectors 1.

A connector not shown in the drawings is provided in the detector storage 26, and connected to a connector 16a of the detector 1 when the detector 1 is stored.

[1-3. Console]

The console 3 is configured by including a PC, a mobile terminal, or a dedicated device.

The console 3 according to the embodiment is mounted on top of the generating device 2, as shown in FIG. 1.

In addition, the console 3 can set, for at least one of the device 1 and the generating device 2, imaging conditions (tube voltage, tube current and irradiation time or current time product (mAs value), imaging area, imaging direction, etc.) based on the imaging orders obtained from other systems (HIS, RIS, etc.) or based on the operations performed on the operation interface 32 by the user U (e.g. radiologist).

In addition, the console 3 can acquire the radiation image data generated by the detector 1, store the acquired data in itself, and transmit the acquired data to other devices (PACS, dynamic state analysis device, etc.).

[1-4. Outline of Radiation Imaging Using Radiation Imaging System]

The radiation imaging (sitting position imaging) using the system 100 (medical cart) configured in such a way is performed as follows.

First, the system 100 is placed in the vicinity of the subject S (on the side of the bed B or wheelchair).

Next, the subject S is caused to be in a sitting posture. If the subject S is seated on an angle-adjustable device (such as a bed B that can be partially erected), the angle of the backrest is adjusted accordingly.

Next, the approximate position and direction of the tube 23 are adjusted so that the radiation port of the tube 23 faces the subject S's imaging target area.

Next, the detector 1 is removed from the detector storage 26 and placed between the hack and the backrest of the subject S.

Next, while referring to inclination information (see below for details), the direction of the tube 23 and the irradiation field are finely adjusted so that the irradiation axis of radiation R is orthogonal to the radiation incidence plane 1a.

Next, imaging is performed (radiation R is emitted to the diagnostic target area of subject S, and a radiation image (static image, dynamic image) of the diagnostic target area is generated in detector 1).

When a dynamic image is imaged, the image data of the dynamic image is sent to a dynamic state analysis device as necessary to analyze the dynamic state of the imaged area (ventilation function/blood flow slate of the lungs, flexion and extension of joints, etc.).

[1-5. Others for Radiation Imaging System]

The generating device body 21 and the console 3 may be integrated (may be contained in a single housing).

In addition, the generating device 2 may be movable by means other than wheels. For example, the generating device 2 may be light enough to be carried by a person or mounted on a commercially available cart, or it may have a smooth bottom surface that slides against the floor.

In addition, in the system 100, one of the detector 1 and the generating device 2 may be installed in the imaging room of a medical facility, etc. (the other of the detector 1 and the generating device 2 may be freely movable).

<2. Details of Radiation Detector>

Next, the details of the detector 1 included in the above system 100 will be described.

Figure 3:
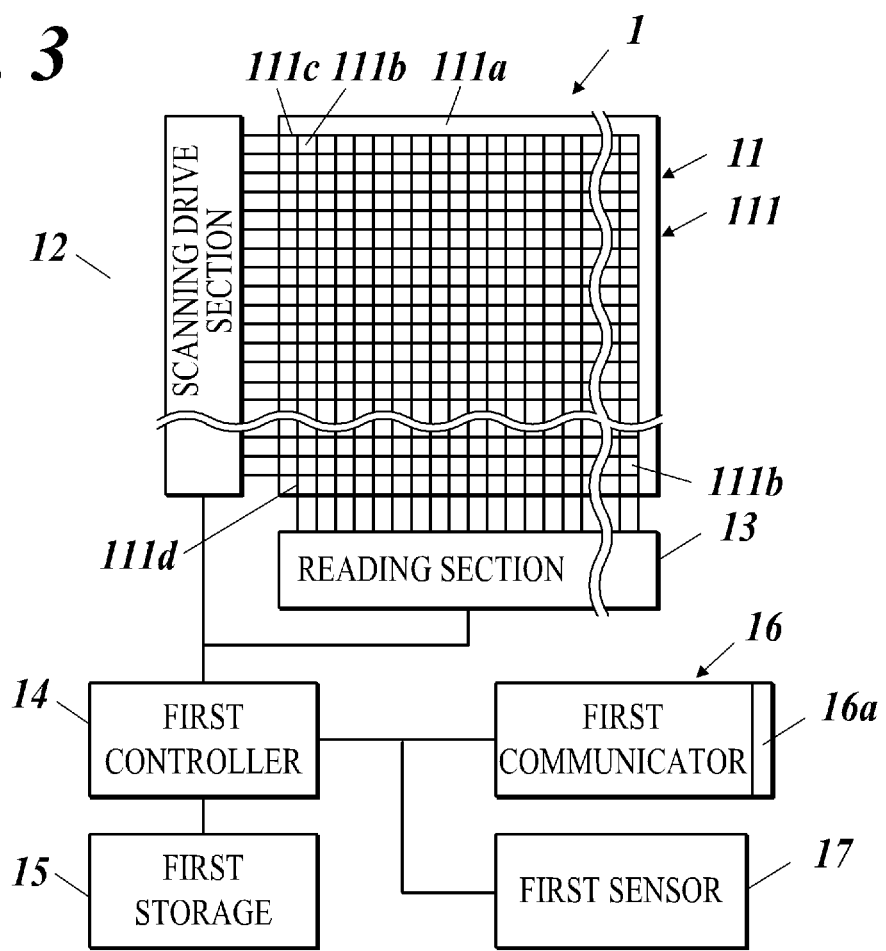
FIG. 3 is a block diagram showing the radiation detector of FIG. 2.

FIG. 3 is a block diagram showing the electrical configuration of detector 1.

[2-1. Specific Configuration of Radiation Detector]

The detector 1 includes, as shown in FIG. 3, a radiation detecting section 11, a seaming drive section 12, a reading section 13, a first controller 14, a first storage 15, a first communicator 16, and a first sensor 17.

These components 11 to 17 are electrically connected.

[2-1-1. Sensor]

The radiation detecting section 11 includes a scintillator not shown in the drawings and a photoelectric conversion panel 111.

The scintillator is formed to be a flat plate by, for example, a columnar crystal of CsI.

The scintillator is designed to emit electromagnetic waves (e.g., visible light) with a longer wavelength than that of the radiation at an intensity corresponding to the dose (mAs) of radiation received by receiving the radiation.

The scintillator is arranged to spread parallel to the radiation incidence plane 1a of the housing (see FIG. 2).

The photoelectric conversion panel 111 is arranged to spread parallel to the scintillator, on the opposite side to the face facing the radiation incidence plane 1a in the scintillator.

The photoelectric conversion panel 111 includes a base, 111a and multiple charge accumulating sections 111b.

The multiple charge accumulating sections 111b are arranged two dimensionally (for example, in matrix) according to the respective pixels of the radiation image on the face facing the scintillator in the base.

The charge accumulating sections 111b respectively include semiconductor elements that generate charges of the amounts corresponding to the intensities of electromagnetic waves generated by the scintillator and switch elements that are provided between the respective semiconductor elements and wirings connected to the reading section 13.

A bias voltage is applied to each of the semiconductor elements from a power supply circuit not shown in the drawings.

The charge accumulating sections accumulate and release the charges to be read out as signal values according to the received radiation by switching on/off of the switch elements.

[2-1-2. Scanning Drive Section]

The scanning drive section 12 is capable of switching each switch element to the on or off state by applying an on or off voltage to each scanning line 111c of the radiation detecting section 11.

[2-1-3. Reading Section]

The reading section 13 reads the amount of charge that has flowed in from the charge accumulating section 111b through each signal line 111d of the radiation detecting section 11 as a signal value.

The reading section 13 may perform binning when reading out the signal value.

[2-1-4. Controller]

The first controller 14 includes a CPU (Central Processing Unit) and a RAM (Random Access Memory), which are not shown in the drawings.

The CPU reads the various processing programs stored in the first storage 15, expands them to RAM, and executes various processes according to the processing programs to control the operation of the various parts of the detector 1 in a comprehensive manner.

The first controller 14 generates image data of the radiation image based on the multiple signal values read by the reading section 13.

[2-1-5. Storage]

The first storage 15 is composed of HDD (Hard Disk Drive), semiconductor memory, etc.

The first storage 15 stores the various programs executed by the first controller 14, as well as the parameters and files necessary for executing the programs.

The first storage 15 may be capable of storing the image data of the radiation image.

[2-1-6. Communicator]

The first communicator 16 is composed of communication modules and other devices.

The first communicator is capable of sending and receiving various signals and data to and from other devices (detector 1, the console 3, etc.) wired or wirelessly connected via a communication network.

[2-1-7. First Sensor]

The first sensor 17 detects information necessary for calculating the inclination information.

The first sensor 17 according to the embodiment is a 3-axis acceleration sensor.

The 3-axis acceleration sensor detects each of the accelerations acting in three axis (X-axis, Y-axis and Z-axis) directions as information for calculating the inclination information, and sends them to the first controller 14.

In the stationary state, only gravitational acceleration acts on the 3-axis acceleration sensor. Therefore, the 3-axis acceleration sensor detects each of the three axial components of the gravitational acceleration in the stationary state.

The first sensor 17 may be a 6-axis sensor or a 9-axis sensor.

The 6-axis sensor is a 3-axis acceleration sensor with an additional function to detect the angular velocity (gyro) of each of the three axes.

The 9-axis sensor is a 6-axis sensor with an additional function to detect the direction (east, west, north, and south) of each of the three axes.

[2-2. Specific Operations of Radiation Detector]

The first controller 14 of detector 1 configured in this way is designed to operate as follows.

[2-2-1. Detect and Send Acceleration]

For example, the first controller 14 causes the first sensor 17 to repeatedly detect the 3-axis component of gravitational acceleration when a predetermined condition is fulfilled.

The predetermined conditions include, for example, that the power of the detector 1 is turned on, that a predetermined control signal is received from another device (the generating device 2, the console 3, etc.), and that a predetermined operation is performed on an operation interface of the detector 1.

Whenever the first sensor 17 detects the 3-axis component of gravitational acceleration, the first controller 14 sends the detected 3-axis component of gravitational acceleration to the generating device 2 via the first communicator 16.

[2-2-2. Generate and Send Radiation Image]

The first controller 14 controls the scanning drive section 12 to accumulate and emit electric charges in the radiation detecting section 11 in synchronization with the timing when radiation R is emitted from the generating device 2.

In addition, the first controller 14 controls the reading section 13 to read out the signal value based on the charge emitted by the radiation detecting section 11.

In addition, the first controller 14 generates the radiation image according to the dose distribution of the emitted radiation R, on the basis of the signal value read by the reading section 13.

In the case of generating a still image, the radiation image is generated only once per pressing of the irradiation instruction switch 22.

In the case of generating a dynamic image, the generation of frame constituting the dynamic image is repeated multiple times (e.g., 15 times per second) per specified time per pressing of the irradiation instruction switch 22.

The first controller 14 sends the generated image data of the radiation image to another device (the console 3, dynamic state analysis device, etc.) via the first communicator 16.

[2-3. Other 1 for Radiation Detector]

The radiation detecting section 11 of detector 1 may not include a scintillator, and a semiconductor device may directly generate an electric charge by receiving radiation.

The detector 1 may also display the generated dynamic image in real time on a display device connected to itself (e.g., fluoroscopy), instead of in the form of image data.

[2-4. Other 2 for Radiation Detector]

The first sensor 17 (3-axis acceleration sensor) of detector 1 outputs in some cases an output value indicating a slight inclination even when the radiation incidence plane 1a is parallel to the ideal horizontal plane due to the mounting condition on the base 111a of the radiation detecting section 11, etc., the mounting condition of the radiation detecting section 11 in detector 1, the distortion of the housing of detector 1, etc.

In addition, when the detector 1 is carried, the above effect that causes the output value to indicate an inclination may newly occur or the degree of the above effect may change if the detector 1 is subjected to a shock (e.g., dropped).

Therefore, the first controller 14 may correct (calibrate) the detected value of the first sensor 17 that is output to the generating device 2.

Specifically, the first controller 14 corrects the output value to indicate that there is no inclination when the detector 1 is placed on an ideal horizontal plane.

Or, the first controller 14 corrects the output value to indicate that the detector is inclined at a known inclination angle when it is stored in a location where the inclination angle relative to the ideal horizontal plane is known (e.g., in the detector storage 26 of the medical cart).

The first controller 14 then stores the corrected data obtained from the correction in the first storage 15.

The correction is performed, for example, when the detector 1 is initially installed, when the detector 1 has been shocked, or when the corrected data is not stored in the first storage 15 of the detector 1.

The first controller 14 may automatically perform the correction when it detects that the detector 1 has been stored in the detector storage 26.

In addition, the first controller 14 may prompt the user U to perform the correction (e.g., by displaying text to prompt the user). In this case, the correction may be prompted only when it is determined that the magnitude of the deviation of the calculated first angle information from a specified value of the rotation angle with respect to the horizontal plane when the detector storage 26 stores the detector 1 exceeds an allowable range.

<3. Details of Radiation Generating Device and Console>

Next, the details of the generating device 2 and the console 3 provided in the above system 100 will be described.

Figure 4:
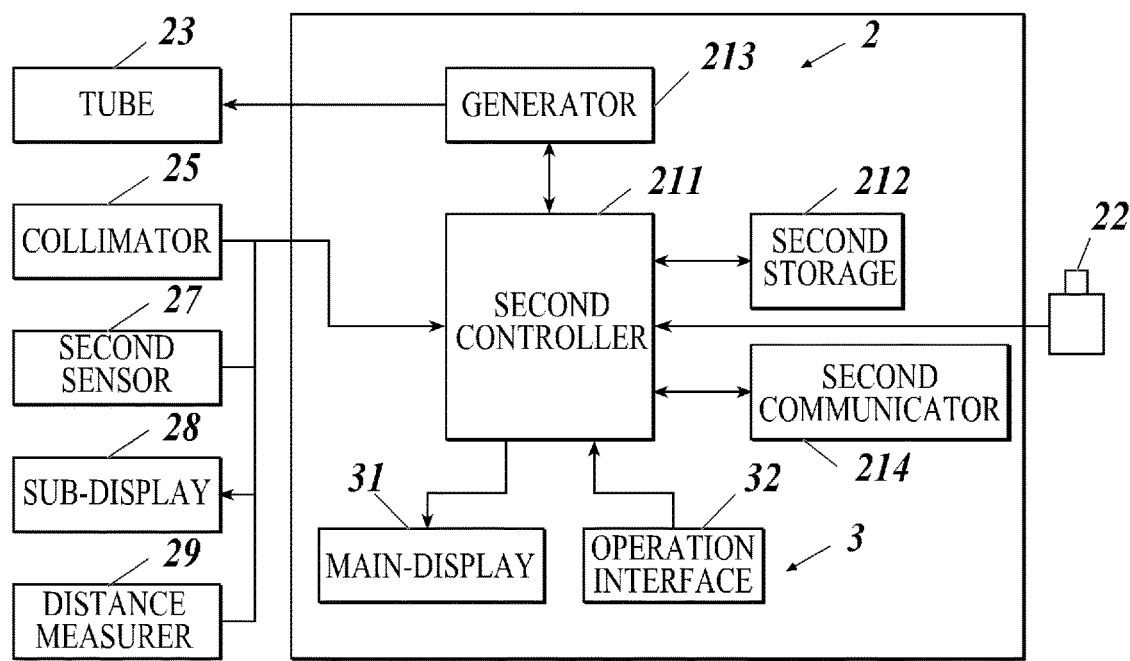
FIG. 4 is a block diagram showing the radiation generating device and the console of the radiation imaging system of FIG. 1.
Figure 5:
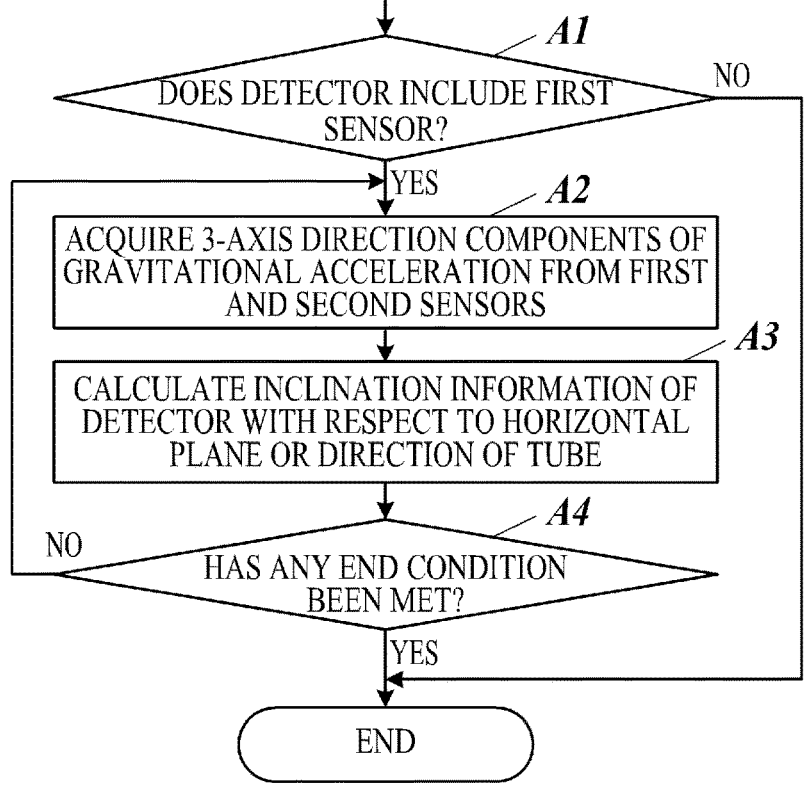
FIG. 5 is a flowchart showing the flow of inclination information preparation processing performed by the radiation generating device in FIG. 4.
Figure 6A:
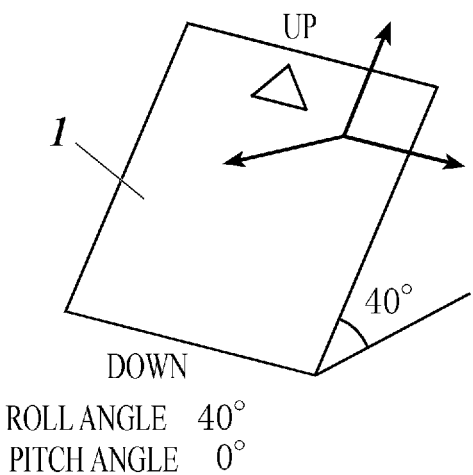
FIGS. 6A to 6C are views each showing placement of the radiation detector 1 and inclination information when the radiation detector 1 is placed.
Figure 6B:
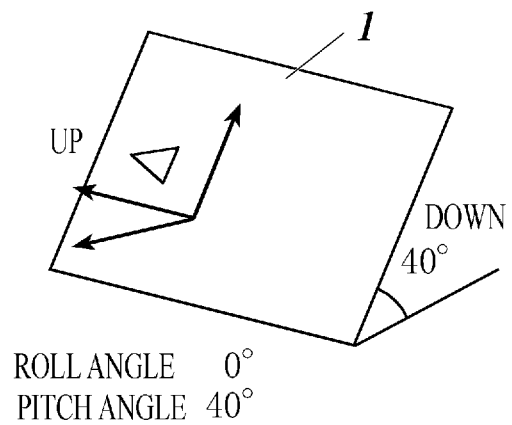
Figure 6C:
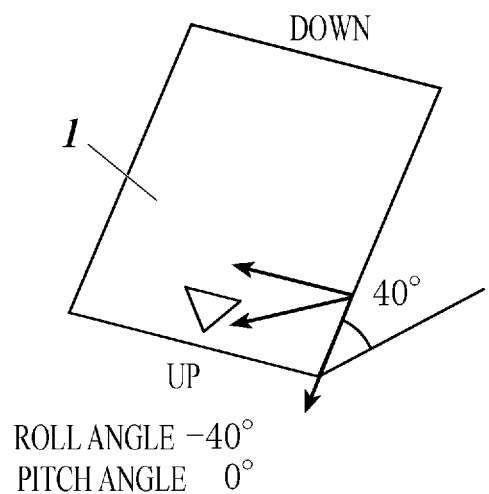
Figure 7:
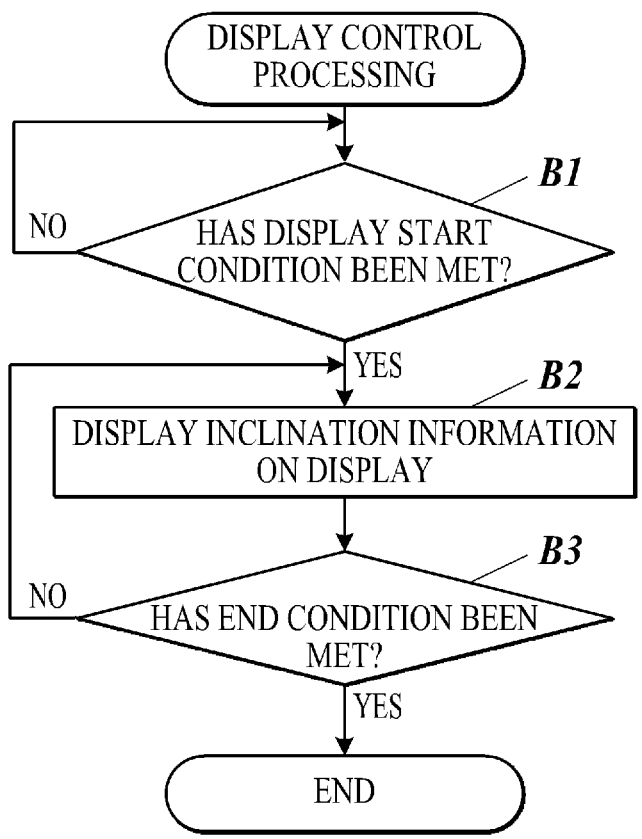
FIG. 7 is a flowchart showing the flow of display control processing performed by the radiation generating device in FIG. 4.

FIG. 4 is a block diagram showing the electrical configuration of the generating device 2 and the console 3, FIG. 5 is a flowchart showing the inclination information preparation processing flow executed by the generating device 2, and FIGS. 6A to 6C are diagrams each showing the placement of the detector 1 and the inclination information when the detector 1 is placed, FIG. 7 is a flowchart showing the flow of display control processing executed by the generating device 2, and FIGS. 8 to 11A and 11B show an example of the screen displayed by the generating device 2 or the console 3.

[3-1. Specific Configuration of Radiation Generating Device]

The generating device 2 includes, for example, a second sensor 27, a sub-display 28, and a distance measurer 29 as shown in FIG. 4, in addition to the above generating device body 21, irradiation instruction switch 22, tube 23, tube supporter 24, collimator 25, and detector storage 26.

The generating device body 21 of the generating device 2 includes a second controller 211 (a hardware processor), a second storage 212, a generator 213, and a second communicator 214.

The components 22, 23, 25, 27, 28 and 211 to 214 are electrically connected to each other via a bus.

[3-1-1. Second Sensor]

The second sensor 27 according to the embodiment is a 3-axis acceleration sensor similarly to the first sensor 17.

The second sensor 27 may be a 6-axis sensor or a 9-axis sensor.

The sensor forming the second sensor 27 may be of a different type from that of the sensor forming the first sensor 17.

[3-1-2. Sub Display]

The sub-display 28 is composed of a monitor such as an LCD (Liquid Crystal Display) or CRT (Cathode Ray Tube).

The sub-display 28 is designed to display various images and information according to the instructions of the display signal input from the second controller 211.

The sub-display 28 according to the embodiment is provided in the housing of the collimator 25.

The sub-display 28 may be provided in the housing of the tube 23 or in the tube supporter 24.

[3-1-3. Distance Measurer]

The distance measurer 29 measures the SID or SSD.

The SID (source image distance) is the distance between the focus F of radiation R and the imaging surface 11a of detector 1 (the surface where the charge accumulating section 111b is installed in the radiation detecting section 11).

The SSD (source skin distance) is the distance between the focus F of radiation R and the subject's body surface, and is approximately equal to the difference between the SID and the subject's body thickness.

The distance measurer 29 according to the embodiment is provided in the collimator 25.

The distance measurer 29 may, for example, consist of a light emitter that emits a laser light, a detector that detects the reflected laser light, and a calculator that calculates the distance from the light emitter to the reflection point based on the time between the emission of the laser light and the detection of the reflected laser light. The distance measurer 29 may also consist of an optical camera that images the detector 1 in the radiation direction, and a calculator that calculates the SID based on the optical image of the detector 1 generated by the optical camera and the size information of the detector 1. The distance measurer 29 may also consist of a combination of them.

Since the laser light is reflected by the body surface of subject S, the distance measured by the distance measurer 29 using the laser light is often. SSD, In this case, the value obtained by adding the subject S's body thickness to the measured SSD is used as the SID.

The body thickness may be a predetermined standard value, a value entered by the user, or a value automatically calculated from the subject S's information.

[3-1-4. Second Controller]

The second controller 211 is composed of a CPU, RAM, etc.

The CPU of the second controller 211 reads various programs stored in the second storage 212, expands them in the RAM, executes various processes according to the expanded programs, and centrally controls the operation of each component of the generating device 2.

[3-1-5. Second Storage]

The second storage 212 is composed of a non-volatile memory, hard disk, etc.

In addition, the second storage 212 stores various programs executed by the second controller 211, parameters necessary for executing the programs, files, etc.

[3-1-6. Generator].

The generator 213 applies a voltage according to the preset imaging conditions to the tube 23 and energizes a current according to the imaging conditions to the tube 23 upon receiving an imaging instruction signal from the second controller 211.

[3-1-7. Second Communicator]

The second communicator 214 is composed of communication modules and other devices.

The second communicator 214 is capable of sending and receiving various signals and data to and from other devices (detector 1, console 3, etc.) wired or wirelessly connected via a communication network.

[3-2. Specific Configuration of Console]

The console 3 includes a controller, a storage, a communicator, a main-display 31, and an operation interface 32.

The second controller 211, second storage 212, and second communicator 214 of the generating device 2 also respectively serve as the controller, storage, and communicator of the console 3 according to the embodiment.

The console 3 may have its own controller, storage and communicator.

[3-2-1. Main-Display]

The main-display 31 is composed of a monitor such as an LCD or CRT.

The main-display 31 displays various images and information according to the instructions of the display signal input from the second controller 211,

[3-2-2. Operation Interface]

The operation interface 32 is configured to be operable by the user.

The operation interface 32 includes, for example, a keyboard (cursor keys, numeric input keys, various function keys, etc.), a pointing device (mouse, etc.), and a touch panel laminated on the surface of the main-display 31.

The operation interface 32 outputs control signals to the second controller 211 according to the operations performed by the user.

[3-3. Specific Operation of Radiation Generating Device and Console]

The second controller 211 of the generating device 2 (the console 3), configured as described above, operates as follows.

[3-3-1. Calculation of Inclination Information]

The second controller 211 executes inclination information preparation processing as shown in FIG. 5, for example, when a predetermined condition is fulfilled.

The predetermined conditions include, for example, that the power of the generating device 2 is turned on, that communication with the detector 1 is enabled, and that the operation interface 32 of the console 3 is operated.

(First Confirmation Process)

In this inclination information preparation processing, the second controller 211 first executes the confirmation process (Step A1).

In this confirmation process, the second controller 211 determines the information of the detector 1 connected to itself (registered in the console 3).

Specifically, the second controller 211 confirms whether or not the detector 1 includes the first sensor 17.

More specifically, the second controller 211 confirms whether or not the detector 1 includes the first sensor 17, for example, by referring to the presence/absence information of the first sensor 17 stored in the detector 1, the detector ID stored in the detector 1 and comparison information of the detector 1 and the presence/absence of the first sensor 17 stored in other devices (such as the console 3), etc.

In this confirmation process, if it is determined that the detector 1 does not include the first sensor 17 (Step A1: No), the second controller 211 ends the angle calculation process (does not allow displaying of the inclination information).

On the other hand, if it is determined that the detector 1 includes the first sensor 17 (Step A1: Yes), the second controller 211 proceeds to the next process (Step A2) (allows displaying of the inclination information).

By the second controller 211 executing this confirmation process, the inclination information will not be displayed when using a detector that does not include the first sensor 17, thus preventing the user U from misidentification.

When using the detector 1, which includes the first sensor 17, the inclination information is displayed, allowing the user U to perform detailed positioning.

Acquisition Process

If at least one of the above conditions is determined to be fulfilled in the above condition determination process, the second controller 211 executes the acquisition process (step A2).

In this acquisition process, the second controller 211 obtains the 3-axis direction component of the gravitational acceleration detected by the first sensor 17 from the detector 1.

In addition, in this confirmation process, the second controller 211 obtains the 3-axis direction component of the gravitational acceleration detected by the second sensor 27 from the second sensor 27.

Calculation Process

After obtaining the 3-axis direction component of the gravitational acceleration, the second controller 211 executes the calculation process (Step A3).

In this calculation process, the second controller 211 calculates the inclination information based on the 3-axis direction component of the gravitational acceleration detected by the first sensor 17 and second sensor 27.

The "inclination information" is the information that indicates the inclination of the detector 1 with respect to the horizontal plane or the direction of tube 23.

Specifically, the second controller 211 calculates the rotation angle (roll angle $\Psi$ and pitch angle $\theta$) of the detector 1 with respect to the horizontal plane as the first angle information.

In addition, the second controller 211 calculates the rotation angle (roll angle $\Psi$ and pitch angle $\theta$) of the tube 23 with respect to the horizontal plane as the second angle information based on the 3-axis direction component of the gravitational acceleration detected by the second sensor 27.

In the case where the inclination information is information indicating the inclination of detector 1 with respect to the horizontal plane, the second controller 211 uses the calculated first angle information as the inclination information.

On the other hand, in the case where the inclination information is information indicating the inclination of the detector 1 with respect to the tube direction, the second controller 211 calculates the difference between the calculated first angle information and second angle information, and uses the difference as the inclination information.

The calculation of the first angle information may be performed by the first sensor 17 or the first controller 14.

Also, the second sensor 27 may perform the calculation of the second angle information.

When the detector 1 to be used is a half-cut size (14 inch×17 inch), the detector 1 is usually used in the state shown in FIG. 6A, but depending on the physique of the subject S, imaging may be performed by rotating the detector 1 by 90 degrees, as shown in FIG. 6B.

Also, since the detector 1 has a simple panel shape, the user U may not be aware of the up and down of the detector 1, and may perform imaging with the upside-down (rotated 180 degrees) as shown in FIG. 6C (the radiation image generated is also upside-down, but can be rotated later.)

When calculating the inclination information of the detector 1 using the 3-axis acceleration sensor, it is common to calculate the roll angle $\Psi$ and pitch angle $\theta$ with respect to the horizontal plane.

Therefore, if the detector 1 is rotated as described above, the relationship between the roll angle $\Psi$ and pitch angle $\theta$ will be reversed, or the roll angle $\Psi$ or pitch angle $\theta$ will be calculated as negative values. This may cause problems when trying to finely adjust the roll angle $\Psi$ and pitch angle $\theta$ of the tube 23.

In many cases, imaging is performed under the condition that the pitch angle $\theta$ of detector 1 is almost 0 degrees.

Thus, in this calculation process, the second controller 211 may calculate the magnitude of the angle $\varphi$ between the horizontal plane and the radiation incidence plane of detector 1 as inclination information.

Specifically, the second controller 211 converts the 3-axis direction component of the gravitational acceleration into the angle (the angle $\varphi$ between the horizontal plane and the radiation incidence plane 1a) between a straight line orthogonal to the radiation incidence plane 1a of detector 1 and a vertical line (Z-axis), by using the general formula for converting the general orthogonal coordinate system to a spherical coordinate system.

In this way, the direction of the tube 23 can be easily finely adjusted because the inclination information can be managed by a single index. Specifically, after adjusting the pitch angle $\theta$ of the tube to be 0 degrees, the roll angle $\Psi$ of the detector and the roll angle $\Psi$ of the tube 23 are adjusted to match each other.

Even when the detector 1 is rotated on the axis orthogonal to the imaging surface the inclination information does not change, which makes it possible to perform displaying close to the sensation of the user U. As a result, fine adjustment of the position and direction of the tube 23 can be easily performed without being conscious of the rotation of the detector 1.

The second controller 211 may use the maximum absolute values of the calculated roll angle $\Psi$ and pitch angle $\theta$ as inclination information.

In this way, the above-mentioned angle $\varphi$ can be calculated using a simpler method.

The second controller 211 may determine whether or not the imaging surface 11a of the detector 1 is facing upward after calculating the inclination information or the angle $\varphi$ between the horizontal plane and the radiation incidence plane 1a in the above calculation process.

Specifically, the second controller 211 judges that the imaging surface 11a is facing upward (normal) when the inclination information or the angle $\varphi$ is less than 90 degrees, and judges that the back side is facing upward (abnormal) when the angle $\varphi$ exceeds 90 degrees.

In the case where the inclination information or the angle $\varphi$ is near 90 degrees, the second controller 211 may determine that the backside is facing up if the angle is greater than 90 degrees (e.g., 110 degrees), because the surface that is determined to be facing up may wobble.

The second controller 211 may alert the user U (e.g., display a wanting) if the second controller 211 determines that detector 1 is placed with the front and back sides reversed.

After detector 1 is placed under or behind the subject S, it is not possible to notice whether the front and back sides of detector 1 are reversed until imaging is finished. However, in this way, it is possible to check whether the front and back sides of detector 1 are not reversed even when the detector 1 is placed under or behind the subject S. This prevents the subject S from being unnecessarily exposed due to failure of imaging.

The second controller 211 according to the embodiment sexes as a calculator by executing the calculation process described above.

In the inclination information preparation processing according to the embodiment, after calculating the inclination information, the second controller 211 executes the end determination process (Step A1).

In the end determination process according to the embodiment, the second controller 211 determines whether at least one of the following end conditions (1) and (2) has been fulfilled.

(1) The irradiation instruction switch 22 has been operated.

(2) The emission of radiation R has been completed.

The above (1) and (2) are the end conditions since the radiation image to be generated is fixed when radiation R is emitted, and there is little need to continue the inclination information preparation processing and display control processing described below.

In this end determination process, if it is determined that the end conditions have not been met (fulfilled) (Step A4: No), the second controller 211 returns to the process of Step A2. In other words, the second controller 211 repeats the acquisition of the first angle information and the calculation of the inclination information until any of the end conditions is fulfilled.

On the other hand, if it is determined that any of the end conditions is met (fulfilled) (Step A4: Yes), the second controller 211 ends the inclination information preparation processing.

(Other 1 for Inclination Information Preparation Processing)

After calculation of inclination information in the above inclination information preparation processing, the second controller 211 may execute state determination processing.

In the state determination processing, the second controller 211 determines whether the difference between the first angle information and the second angle information is within a predetermined reference range.

In that case, the second controller 211 may use the result of the determination as the inclination information.

The second controller 211 may also determine whether or not the SID measured by the distance measurer 29 is within a predetermined reference range.

In the case where the state determination processing is performed, the second controller 211 may determine whether dynamic imaging is included in the imaging order before performing the state determination processing.

If it is determined that dynamic imaging is included in the imaging order, the second controller 211 may change (narrow) the reference range to be used in the subsequent state determination processing, since the accuracy of alignment required for dynamic imaging is higher than the accuracy of alignment required for imaging of still images due to the dynamic imaging being used for dynamic analysis.

When the state determination processing is performed, the second controller 211 may change the reference range according to the presence or absence of a grid and its type.

This is because the larger the grid ratio is, the more the obliquity of radiation R influences (the influence of cutoff by the grid causes density differences in the radiation image).

(Other 2 for Inclination Information Preparation Processing)

In the inclination information preparation processing, the second controller 211 may calculate the inclination information based on multiple pieces of first and second angle information obtained by the first sensor 17 detecting the 3-axis direction component of the gravitational acceleration multiple times each time the predetermined time elapses.

Specifically, the second controller 211 executes the calculation process once for each multiple executions of the above acquisition process, and calculates the average value, median value, etc. of the multiple, pieces of first and second angle information as the inclination information in the calculation process.

After the detector 1 is placed under or behind the subject 5, the angle display will fluctuate due to the effect of the subject S's breathing, etc. However, in the above way, the variation of inclination information due to breathing, etc. can be reduced.

In addition, by reducing the variation of inclination information, fine adjustment of the direction of the tube 23 can be easily performed.

[3-3-2. Display Control of Inclination Information]

The second controller 211 executes display control processing as shown in FIG. 7, for example, when repeating of the above acquisition process and calculation process are started.

The second controller 211 executes this display control processing in parallel with the above inclination information preparation processing.

(Condition Determination Process)

In this display control processing, the second controller 211 first executes the condition determination process (Step B1).

In the condition determination process according to the embodiment, the second controller 211 determines whether or not at least one of the following display start conditions (1) to (5) has been fulfilled.

(1) Imaging order is selected on the console to indicate the start of imaging.

(2) The detector 1 is removed from the storage location (the detector storage 26 the system 100 is a medical cart, or the charging cradle if the system 100 is installed in an imaging room, etc.).

(3) The detector 1 is disconnected from the cable.

(4) The predetermined button on the collimator 25 (e.g., the lamp button to emit visible light to the area that will be the radiation field of radiation R) provided with the tube is operated.

(5) The magnitude of the inclination of detector 1 is within a reference range (e.g., the angle difference between the tube 23 and detector 1 is smaller than a specified angle).

In this condition determination process, if it is determined that none of the above plural display start conditions have been met (fulfilled) (Step B1: No), the second controller 211 repeats this condition determination process (waits until a display start condition is fulfilled).

On the other hand, if it is determined that at least one of the above plural display start conditions has been met in the condition determination process (Step B1: Yes), the second controller 211 proceeds to the next process (Step B2).

While adjusting the rough position and direction of the tube 23, the detector 1 is not yet placed under or behind the subject 5, and the inclination information may not be helpful. Displaying the inclination information at such a timing may cause confusion to the user LI (e.g., adjusting the direction of the tube 23 to match the angle of the detector 1, which has not yet been accurately positioned). However, by the second controller 211 executing this condition determination process, at least one of the main-display 31 and the sub-display 28 displays the inclination information after at least one of the above multiple display start conditions is fulfilled. This prevents the user U from being confused.

In addition, while the collimator 25 is emitting the visible light, the detector 1 is often placed under or behind the subject S since it is in the final stage of the positioning operation. Therefore, if the second controller 211 proceeds to the next process (step B2) when the display start condition (4) is fulfilled, it is possible to provide the user U with useful inclination information at a more appropriate timing.

In this condition determination process, the following display start conditions (6) to (8) may be included in the display start conditions to determine whether the condition is fulfilled or not.

(6) After the detector 1 is removed from the detector storage 26 (the inclination starts to change), the inclination of the detector 1 is stabilized again (the detector 1 is placed under or behind the subject S and does not move).

(7) The detection value of the barometric pressure sensor, which detects the air pressure inside the housing of detector 1, exceeds a reference value (the detector 1 is placed under or behind the subject S and the housing is pressed).

(8) The detector 1 is captured in the optical image generated by the optical camera of distance measurer 29.

By proceeding to the next process (step B2) when the display start condition (6) or (7) is fulfilled, the second controller 211 causes the sub-display 28 and/or the main-display 31 to display the inclination information after the detector 1 is placed under or behind the subject S, thus preventing the user U from being confused.

In addition, the fact that the detector 1 is captured in the area where the optical camera of distance measurer 29 is imaging is considered to mean that the detector 1 is to be placed under or behind the subject S immediately after the detector 1 is captured in the above area. Therefore, by proceeding to the next process when the display start condition (8) is fulfilled, the second controller 211 can display the inclination information on the sub-display 28 and/or the main-display 31 at almost the same timing as proceeding to the next step when the display start condition (6) or (7) is fulfilled, thus preventing the user U from being confused.

(Display Process)

After determining that the display start condition is fulfilled in the condition determination process, the second controller 211 executes the display process (step B2).

In this display process, the second controller 211 causes at least one of the main-display 31 and the sub-display 28 to display the inclination information calculated in the calculation process of the inclination information preparation processing.

Figure 8:
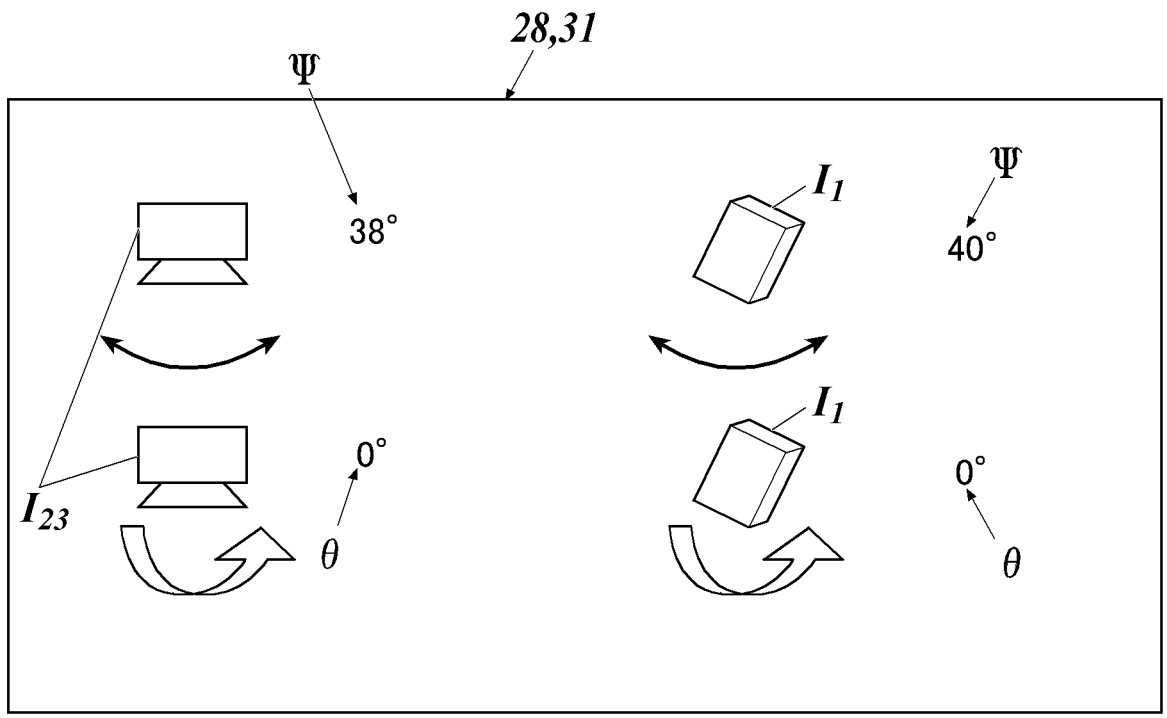
FIG. 8 is au example of a screen displayed by the radiation generating device or the console m FIG. 4.

Specifically, as shown in FIG. 8, for example, the icon $I_{23}$ indicating the tube 23, the roll angle $\Psi$ and the pitch angle $\theta$ of the tube 23, and the icon indicating the detector 1, the roll angle $\Psi$ and the pitch angle $\theta$ of the detector 1 are respectively displayed.

If the inclination information is displayed on the sub-display 28, the user C can refer to the inclination information on the spot when finely adjusting the position and direction of the tube 23, thus facilitating the fine adjustment.

On the other hand, if the inclination information is displayed on the main-display 31, the final confirmation regarding whether the positional relationship between the detector 1 and the tube 23 has not changed can be made when the irradiation instruction switch 22 is operated.

The second controller 211 may perform control to display the roll angle $\Psi$ and the pitch angle $\theta$ of the detector 1 in the form of the difference in the roll angle $\Psi$ and the pitch angle $\theta$ with respect to the tube 23.

Figure 9:
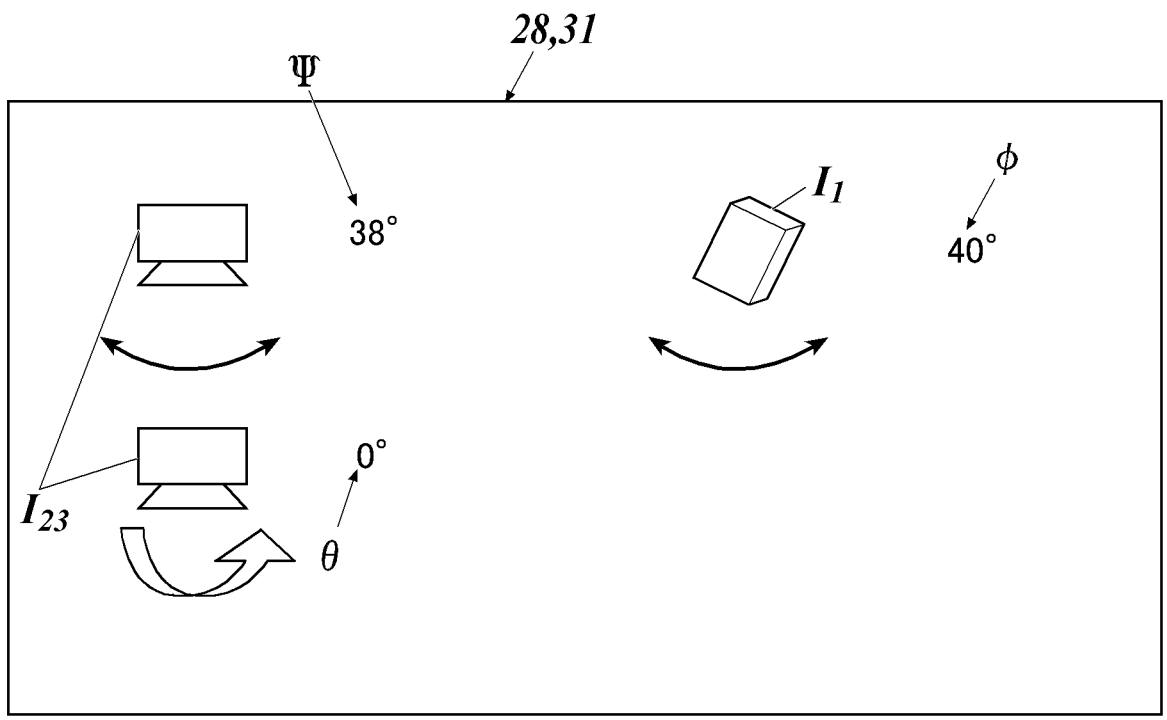
FIG. 9 is an example of a screen displayed by the radiation generating device or the console in FIG. 4.

When the inclination information is the angle $\varphi$ between the horizontal plane and the radiation incidence plane 1a, the second controller 211 may cause the sub-display 28 and/or the main-display 31 to display the roll angle $\Psi$ and the pitch angle $\theta$ of the tube 23 and the angle $\varphi$ between the horizontal plane and the radiation incidence plane 1a respectively, as shown in FIG. 9.

Figure 10A:
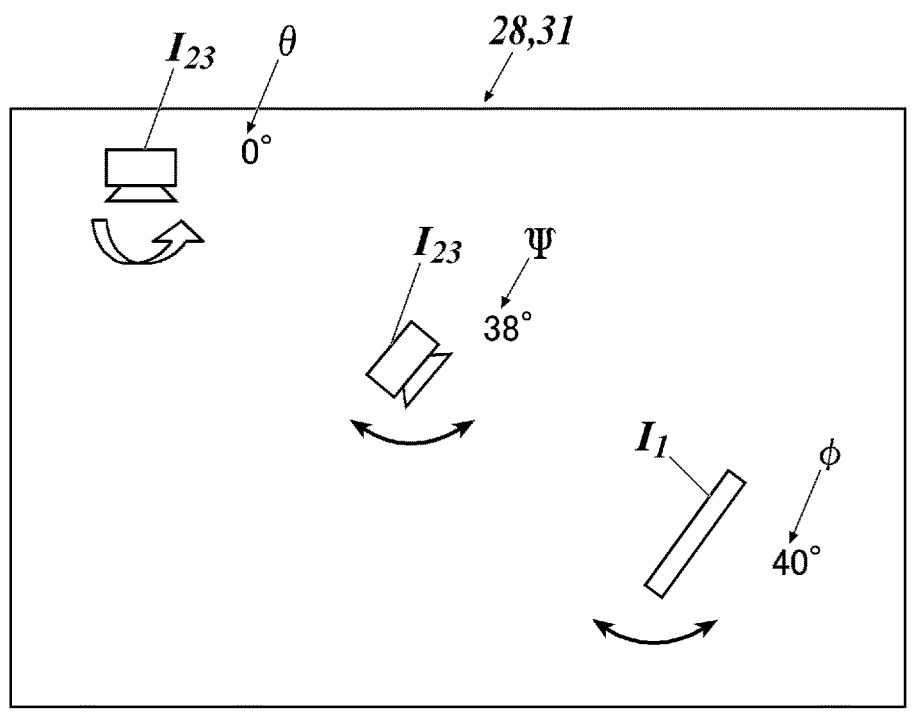
FIGS. 10A to 10B are examples of a screen displayed by the radiation generating device or the console in FIG. 4.

For example, as shown in FIG. 10A, the icon $I_{23}$ which indicates the tube 23 and the icon $I_1$ which indicates the detector 1 may be displayed in the same arrangement as the arrangement when the tube 23 and detector 1 are actually viewed in a plane. In this case, the SID (SSD) measured by the distance measurer 29 may also be displayed.

Figure 10B:
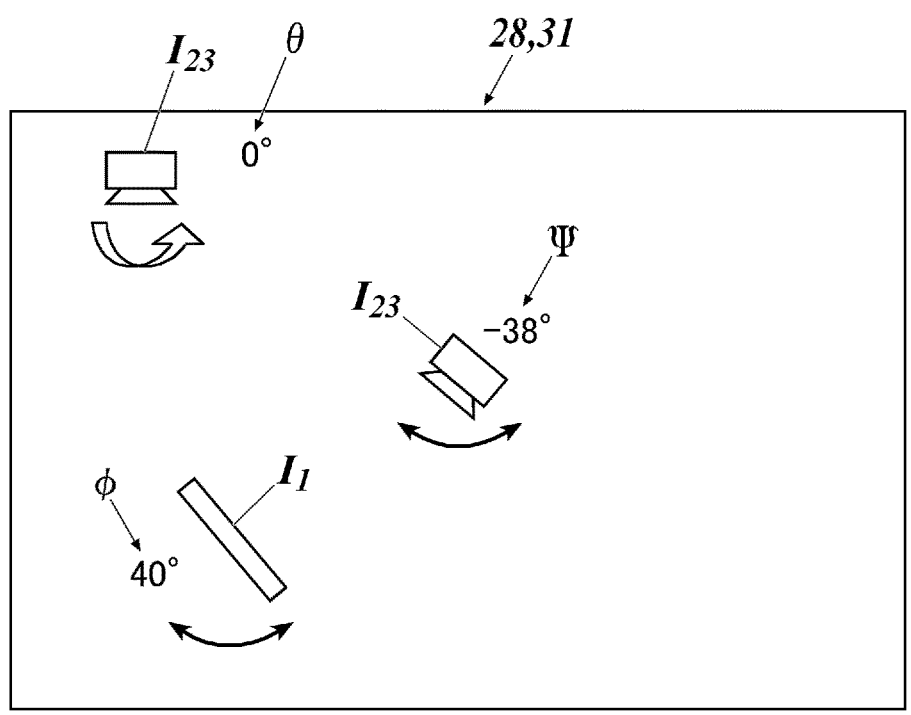

In addition, the sub-display 28 may change its direction in accordance with the change in the direction of the tube 23. For this reason, when the icon $I_{23}$ indicating the tube 23 and the icon $I_1$ indicating the detector 1 are displayed on the sub-display 28, the second controller 211 may change the placement of the icon $I_1$ in response to the change in the direction of the tube 23, as shown in FIG. 10B, for example.

In this case, the second controller 211 may perform control to display the roll angle of the tube 23 in the absolute value. In this way, the angle at which the tube 23 is rotated becomes a positive value, making it easier to match the values.

In the case where the roll angle Ψ is not displayed as the absolute value, this displaying facilitates understanding because the positive/negative of the value matches the positive/negative of the direction in which the tube 23 is rotated.

Figure 11A:
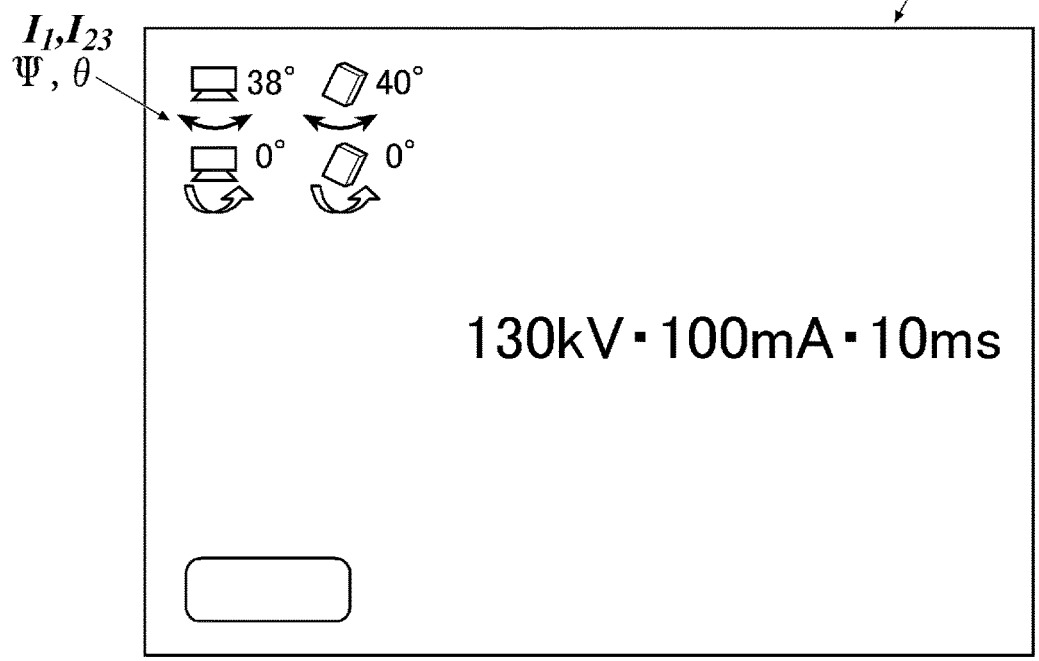
FIGS. 11A to 11B are examples of a screen displayed by the radiation generating device or the console in FIG. 4.
Figure 11B:
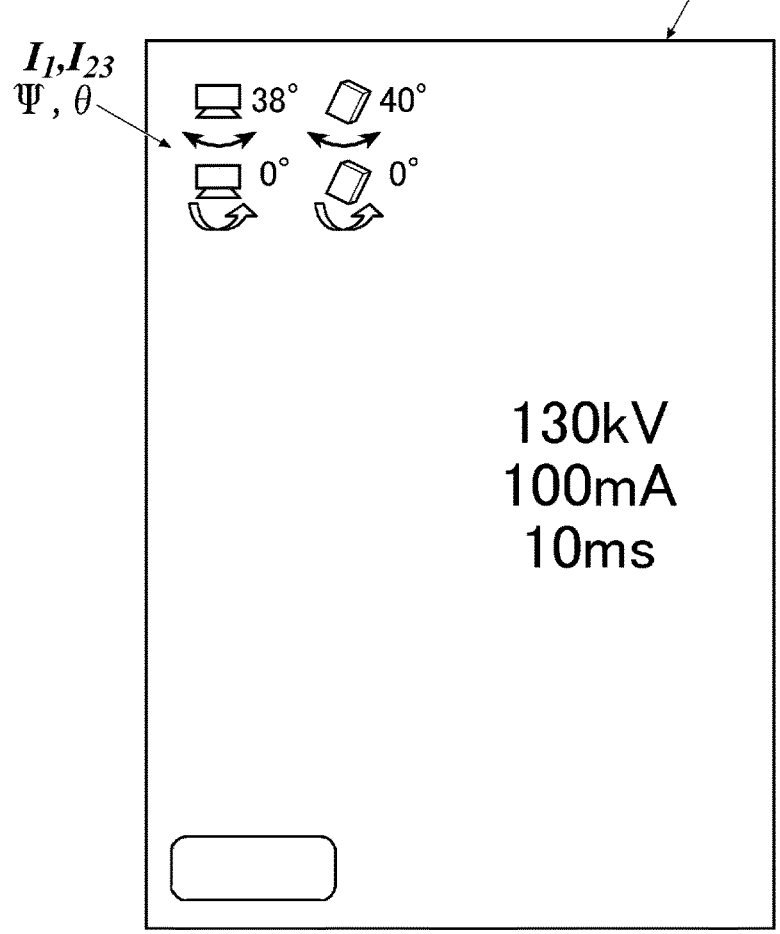

The sub-display 28 rotates with the rotation of the tube 23 and may change to be vertical from horizontal. For this reason, in the horizontal state shown in FIG. 11A, when the tube 23 rotates by a predetermined angle (e.g., more than 45 degrees) and becomes vertical, the second controller 211 may, for example, switch the display screen to vertical as shown in FIG. 11B.

The predetermined angle at which the display screen is switched may be, for example, 70 degrees, etc. In the case of switching at 45 degrees, if the angle of the backrest of the bed B is around 45 degrees in the sitting position imaging, the vertical and horizontal display screens are switched every time the direction of the tube 23 is finely adjusted, and it becomes complicated to check the display contents. Assuming that the angle of the tube 23 in standing imaging is 90 degrees±10 degrees, the angle in laying position imaging is 0 degrees±10 degrees, and the angle in sitting position imaging is 40 degrees±10 degrees, the predetermined angle is preferably 60 to 70 degrees, which is far from the angle in any of the above imaging.

In this case, the display of the icon $I_{23}$ indicating the tube 23 and the icon $I_1$ indicating detector 1 may not be changed. In this way, the user U can be prevented from being confused.

When the angle difference between the tube 23 and detector 1 is within a predetermined range, such switching of the display screen may be restricted. This is because if the vertical and horizontal sides of display screen are switched when the direction of the tube 23 is being finely adjusted, the user U will find it difficult to see the display screen.

Each time the second controller 211 executes the calculation process in the inclination information preparation processing, the second controller 211 updates the inclination information to be displayed to the new one.

In this way, the user U can check the inclination information in real time.

The second controller 211 may cause the sub-display 28 and/or the main-display 31 to display the inclination information before the above display start condition is fulfilled.

In such a case, it is desirable for the second controller 211 to change the display mode of the inclination information as follows:
- Instead of switching of showing/hiding the inclination information, the display color of the inclination information is changed before and after removing the detector 1 from the detector storage 26 (for example, before removing the detector 1 from the detector storage 26, the inclination information is displayed in gray (light color), and after removing the detector 1, the inclination information is displayed in darker (normal) color.)
- Display the fact that the detector 1 is stored in the detector storage 26 or is in the sleep state with the inclination information In this way, the user U can be prevented from being confused as in the case where the inclination information is displayed only after the display start condition is fulfilled.

When a display start condition other than the above display start condition (4) is fulfilled and the system proceeds to the next process (step B2) (i.e., inclination information is displayed before the operation of the specified button of the collimator 25), the second controller 211 may change the display mode of the inclination information to be displayed on the sub-display 28 and/or the main-display 31 while the collimator 25 irradiates the area to be the irradiation field with visible light.

Specifically, the inclination information is made easier to see than before irradiation by enlarging the display or displaying a pop-up window.

When the state determination processing is performed in the above inclination information preparation processing, the second controller 211 may cause the sub-display 28 and/or the main-display 31 to display the result of the determination in the display process. In this way, the user U can easily finely adjust the position and direction of the tube 23.

In this case, only when the state of the tube 23 facing the detector 1 is within a reference range, the second controller 211 may perform control to display this fact, and when the state of the tube 23 facing the detector 1 is out of the reference range, the second controller 211 may not perform control to display this fact. This prevents the user U from being confused. In the case of placing the detector 1 under or behind the subject S after roughly adjusting the position and direction of the tube 23, if the fact that the state of the tube 23 facing the detector 1 is out of the reference range continues to be displayed on the sub-display 28 and/or the main-display 31 while roughly adjusting the position and direction of the tube 23, the user U will be confused.

Also, the second controller 211 may cause the sub-display 28 and/or the main-display 31 to display a predetermined color, and change the color displayed thereon to another color when the state of the tube 23 facing the detector 1 is within the reference range.

In addition, the second controller 211 may output a predetermined sound to the speaker, which is not shown in the drawings, when the state of the tube 23 facing the detector 1 is within the reference range.

The second controller 211 may not display the determination result on the sub-display 28 and/or the main-display 31 for a period of time other than while the collimator 25 is irradiating the area that is the irradiation field with visible light.

During the period when the collimator 25 is not emitting visible light, the detector 1 is often still stored in the detector storage 26 or placed on a desk or the like, whereas during the period when the collimator 25 is emitting visible light, the process is in the final stage of the positioning operation. Thus, by the above configuration, the determination result can be provided to the user U at a more appropriate timing.

In addition, the control on the display of the determination result in the state determination processing which has been described above can also be applied to the determination result of whether the SID (SSD) is within the reference range or not.

In the display control processing according to the embodiment, the second controller 211 executes the end determination process after starting the display of the inclination information (step B3).

In this end determination process, the second controller 211 determines whether or not at least one of the following end conditions (1) to (3) has been fulfilled.
(1) The irradiation instruction switch 22 has been operated.
(2) The irradiation of radiation R is completed.
(3) The inclination information preparation processing is completed.

In this end determination process, if it is determined that none of the end conditions has been met (fulfilled) (step B3: No), the second controller 211 returns to the process of step B2. In other words, the second controller 211 continues to display the inclination information until the end condition is fulfilled.

On the other hand, if it is determined that the end condition is met (fulfilled) (step B3: Yes), the second controller 211 ends the display control processing.

By the second controller 211 executing the display control processing (display control of the sub-display 28 and/or the main-display 31) described above, the sub-display 28 and/or the main-display 31 start or stop displaying of the inclination information that indicates the inclination of detector 1 with respect to the horizontal plane or the direction of tube at a predetermined timing.

In other words, the second controller 211 according to the embodiment is a display controller.

(Other 1 for Display Control Processing)

Before starting the condition determination process in the above display control processing, the second controller 211 may perform a second confirmation process.

In this second condition determination process, the second controller 211 determines whether or not the detector 1 has received an instruction from the console 3 to start imaging.

If there are multiple detectors 1 registered in the console 3 (stored in the detector storage 26), the second controller 211 executes this second confirmation process for each detector 1.

In this case, the second controller 211 causes the sub-display 28 and/or the main-display 31 to display the inclination information of the detector 1 that has received the instruction to start imaging from the console 3 in the subsequent display process.

Conventionally, multiple detectors of different sizes have been installed in the medical cart, but displaying the inclination information of multiple unused detectors at the same time causes confusion to the user U. However, by the second controller 211 executing this second confirmation process, the user U can easily know which of the multiple detectors 1 has the inclination information being currently displayed.

(Other 2 for Display Control Processing)

In the above display control processing, when the second controller 211 causes the sub-display 28 and/or the main-display 31 to display the inclination information before imaging the subject S (during preparation), the second controller 211 may cause the sub-display 28 and/or the main-display 31 to display, together with the inclination information, past inclination information of the past imaging of the subject S.

Specifically, the second controller 211 recalls the past inclination information based on the ID of the subject S and causes the sub-display 28 and/or the min-display 31 to display the past inclination information together.

In this case, it is desirable that the second controller 211 calls the past inclination intonation based on the ID of the subject S and the imaging site (chest, abdomen, etc.) since the manner of inclination of the detector 1 may differ depending on the imaging site.

In the inclinations of the tube 23 and the subject S change at each imaging, there will be differences in the arrangement of internal structures in the subject S and the density of the radiation image. This change may cause minor changes to be overlooked during follow-up. However, by displaying the past inclination information, the reproducibility of positioning can be improved and the risk of missing minor changes can be reduced.

The second controller 211 may perform control to overlay the past inclination information and SID (SSD) on the radiation image. In this way, the limited display space can be effectively utilized and the movement of the eye between the radiation image and past inclination information can be reduced during imaging preparation and diagnosis.

When the imaging currently being prepared is lying position imaging or standing position imaging, the second controller 211 may not cause the sub-display 28 and/or the main-display 31 to display past inclination information. This is because it is obvious that the angle $\varphi$ is between the horizontal plane and the radiation incidence plane 1a is 0° and 90° in lying position imaging and standing position imaging, and displaying this information may confuse the user U.

[3-3-3. Generation of Radiation]

When the second controller 211 receives an operation signal from the irradiation instruction switch 22 (the irradiation instruction switch 22 is operated), the second controller 211 sends an irradiation instruction signal to the generator 213, to instruct the generator 213 to generate radiation R in a manner corresponding to the form of the radiation image to be generated (static image, dynamic image consisting of multiple frames).

The generator 213 which received the irradiation instruction signal from the second controller 211 applies a voltage according to the preset imaging conditions to the tube 23 and energizes the tube 23 with a current according to the imaging conditions.

The tube 23 receives the applied voltage and current from the generator 213, and generates radiation R of a dose corresponding to the applied voltage and current in a manner corresponding to the applied voltage and current.

For still images, the tube 23 emits radiation R only once per pressing of the irradiation instruction switch 22.

In the case of dynamic images, the tube 23 repeats pulsed radiation R irradiation multiple times per predetermined time (e.g., 15 times per second) per pressing of the irradiation instruction switch 22, or continues radiation R irradiation for a predetermined time.

[3-3-4. Storing of Inclination Information]

After generating radiation (imaging), the second controller 211 performs a storing process.

In this storing process, the second controller 211 stores the inclination information at the time of imaging the subject S together with the information about the subject S.

The method of storing the inclination information includes, for example, a method of writing it in the header of the radiation image, a method of storing it in the second storage 212 or in the storage of other devices (such as PACS) while linking it to the radiation image, and so on.

In this storing process, the second controller 211 may store not only the inclination information but also the SID (SSD) at the time the subject S was imaged. In this way, the positions and directions of the detector 1 and the tube 23 at the time of new imaging can be reproduced with a high degree of accuracy because the SID of the subject S when it was imaged in the past can be confirmed when new imaging is performed.

In particular, if the inclination information and the SID are written in the header of the radiation image (if the radiation image and the inclination information are finked), the inclination information can be managed more efficiently, and the inclination information can be made more useful for diagnosis (e.g., it becomes easier for the diagnostician to visualize the arrangement of internal structures as it should be).

In the case of imaging that generates multiple radiation images ma single imaging operation (e.g., dynamic imaging), the second controller 211 may store the inclination information on inclination at the time of image acquisition for each radiation image (frame) in the storing process.

In this way, the user U or the diagnostician can check whether there was a large body movement during imaging by comparing the multiple pieces of inclination information.

In addition, by referring to the inclination information, it is easy to automatically delete abnormal radiation images from the multiple radiation images or exclude them from the analysis.

In addition, by displaying the inclination information together with the radiation images, the diagnostician can be alerted.

In the case where the inclination information at the time of image acquisition is stored for each of the multiple radiation images, the second controller 211 may perform a decision process in the above storing process.

In this decision process, the second controller 211 decides the representative inclination information representing the imaging based on the multiple pieces of inclination information stored for the respective radiation images.

The "inclination information representing imaging" includes, for example, the inclination information at the time of generating a predetermined-numbered (e.g., the first) radiation image among the multiple radiation images, the average value of all pieces of inclination information, time median value of all pieces of inclination information, the average value of part of all pieces of inclination information (e.g., when the first radiation image is generated and when the last radiation image is generated), etc.

The work of handling multiple pieces of inclination information is cumbersome for users U and diagnosticians. However, in this way, only the representative inclination information can be used as a reference for positioning and diagnosis, thus reducing the time and effort required by users U and diagnosticians.

In addition, if the average value, etc., is used as the representative inclination information, the representative inclination information can be made to reflect the imaging status more accurately.

In addition, if the average, median, etc. are used as representative inclination information, the influence of variations in inclination information due to breathing, etc. can be eliminated when used as a reference for positioning and diagnosis.

The second controller 211 according to the embodiment is a storing means (deciding means) by executing the storing process (deciding process) described above.

[3-3-5. Other 1 for Operation of Radiation Generating Device]

The second controller 211 according to the above embodiment is designed to display the inclination information on the sub-display 28 and/or the main-display 31 when the display start condition is fulfilled during the repeated execution of the acquisition process and the calculation process. However, the acquisition and calculation processes can be started when the display start condition is fulfilled. In this way, the power consumption of the second controller 211 can be reduced compared to the case where the acquisition process and the calculation process are executed before the display start condition is fulfilled.

In addition, in this case, the second controller 211 may not display the inclination information on the sub-display 28 and/or the main-display 31 even after the acquisition process and the calculation process are started, but may only store the inclination information. In this way, it is possible to check whether there is an abnormality during imaging by checking the inclination information during maintenance, etc.

[3-3-6. Other 2 for Operation of Radiation Generating Device]

When there are multiple medical carts of the same type, the inclination angle of the detector storage 26 of each medical cart may be slightly different due to individual differences in the distortion of the housing of each medical cart.

Therefore, the second controller 211 may correct (calibrate) the detection value of the first sensor 17 received from the detector stored in the detector storage 26.

Specifically, the second controller 211 of each medical cart corrects the output values to indicate that the rotation angles with respect to the horizontal plane are all the same inclination angle when the detector 1 is stored in the detector storage 26.

<4. Effects>

As described above, the system 100 according to the embodiment includes: the tube 23 that generates radiation R; the detector 1 that generates radiation images according to the received radiation R; and the sub-display 28 and/or the main-display 31 that starts or ends displaying of the inclination information indicating the inclination of the detector 1 with respect to the horizontal plane or the direction of the tube 23 at a predetermined timing.

Thus, according to the system 100, by adjusting the predetermined timing (for example, adjusting the timing to be after the fulfillment (satisfaction) of the display start condition), it is possible to confirm the inclination information at the timing required by the user.

<5. Others>

The present invention is not limited to the above embodiments, and modifications can be made as needed within the scope of the present invention.

For example, the above description discloses an example of using a hard disk, a semiconductor nonvolatile memory and the like as the computer readable medium of the program according to the present invention. However the present invention is not limited to the example. A portable recording medium such as a CD-ROM can be applied as other computer readable medium. A carrier wave is also applied as a medium providing the program data according to the present invention via a communication line.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation imaging system comprising:
a tube that generates a radiation;
a radiation detector to generate a radiation image corresponding to the radiation that is received; and
a display that starts displaying of inclination information indicating an inclination of the radiation detector with respect to a horizontal plane or a direction of the tube in response to fulfillment of at least one of display start conditions which are a display start condition that an imaging order is selected on a console which instructs to start imaging, a display start condition that the radiation detector is removed from a location where the radiation detector is stored, a display start condition that the radiation detector is detached from a cable, a display start condition that a predetermined button of a collimator provided with the tube is operated, and a display start condition that a magnitude of the inclination of the radiation detector is within a reference range.

2. The radiation imaging system according to claim 1, wherein the radiation detector includes a sensor that detects information necessary for calculating the inclination information.

3. The radiation imaging system according to claim 2, further comprising a hardware processor that controls displaying by the display.

4. The radiation imaging system according to claim 1, further comprising a hardware processor in communication with said radiation detector, wherein the hardware processor is configured to determine whether the detector includes a sensor that detects information necessary for calculating inclination information of the radiation detector, wherein the hardware processor controls displaying by the display and allows the displaying of the inclination information when it is determined that the radiation detector includes the sensor and in response to the fulfillment of the at least one of the display start conditions.

5. The radiation imaging system according to claim 1, wherein the display displays the inclination information of the radiation detector that receives an instruction to start the imaging from the console.

6. The radiation imaging system according to claim 1, further comprising a hardware processor that stores the inclination information at a time of imaging of a subject together with information regarding the subject.

7. The radiation imaging system according to claim 6, wherein imaging to generate multiple radiation images per imaging operation is performed, and the hardware processor decides inclination information representing the imaging based on multiple pieces of inclination information that are stored for the respective radiation images.

8. The radiation imaging system according to claim 1, wherein, in displaying of the inclination information before imaging of a subject, the display displays, together with the inclination information, inclination information at a time of past imaging of the subject.

9. The radiation imaging system according to claim 2, further comprising a hardware processor that calculates the inclination information based on multiple pieces of angle information obtained by the sensor performing detection at multiple different times, the sensor detecting the information necessary for calculating the inclination information.

10. The radiation imaging system according to claim 1, further comprising a hardware processor that calculates the inclination information based on multiple pieces of angle information obtained by the sensor performing detection at multiple different times, the sensor detecting the information necessary for calculating the inclination information.

11. The radiation imaging system according to claim 6, wherein the hardware processor calculates the inclination information based on multiple pieces of angle information obtained by the sensor performing detection at multiple different times, the sensor detecting the information necessary for calculating the inclination information.

12. The radiation imaging system according to claim 8, further comprising a hardware processor that calculates the inclination information based on multiple pieces of angle information obtained by the sensor performing detection at multiple different times, the sensor detecting the information necessary for calculating the inclination information.

13. The radiation imaging system according to claim 1, wherein the display ends the displaying of inclination information after fulfillment of at least one of display end conditions consisting of a display end condition that an irradiation instruction switch has been operated and a display end condition that emission of radiation is completed.

14. The radiation imaging system according to claim 1, wherein the display starts displaying the inclination information in response to fulfillment of the display start condition that a magnitude of the inclination of the radiation detector is within a reference range.

15. The radiation imaging system according to claim 1, further comprising a hardware processor in communication with the radiation detector, wherein the hardware processor determines the inclination information, and determines whether a front side of the detector and a back side of the detector are reversed based on the inclination information.

16. The radiation imaging system according to claim 1, wherein the radiation detector includes a first hardware processor that calibrates a detected value of a sensor, the detected value being information necessary for calculating inclination information of the radiation detector, and
the radiation imaging system further comprises a second hardware processor that calculates the inclination information based on the calibrated detected value output by the first hardware processor.

17. A radiation imaging system comprising:
a radiation detector to generate a radiation image corresponding to a radiation that is received;
a hardware processor that calculates inclination information of the radiation detector with respect to a horizontal plane or a direction of a tube which generates the radiation, wherein the hardware processor calculates, as the inclination information, a magnitude of an angle between the horizontal plane and a radiation incidence plane of the radiation detector, and
a display that starts displaying of inclination information indicating an inclination of the radiation detector with respect to a horizontal plane or a direction of the tube in response to fulfillment of at least one of display start conditions which are a display start condition that an imaging order is selected on a console which instructs to start imaging, a display start condition that the radiation detector is removed from a location where the radiation detector is stored, a display start condition that the radiation detector is detached from a cable, a display start condition that a predetermined button of a collimator provided with the tube is operated, and a display start condition that a magnitude of the inclination of the radiation detector is within a reference range.

18. The radiation imaging system according to claim 17, wherein the hardware processor calculates the inclination information based on multiple pieces of angle information obtained by detection that is performed by a sensor each time a predetermined time has elapsed, the sensor detecting information necessary for calculating the inclination information.

19. A radiation imaging method comprising:
generating a radiation by a tube;
generating, by a radiation detector, a radiation image corresponding to the radiation that is received; and
starting displaying by a display of inclination information indicating an inclination of the radiation detector with respect to a horizontal plane or a direction of the tube in response to fulfillment of at least one of display start conditions which are a display start condition that an imaging order is selected on a console which instructs to start imaging, a display start condition that the radiation detector is removed from a location where the radiation detector is stored, a display start condition that the radiation detector is detached from a cable, a display start condition that a predetermined button of a collimator provided with the tube is operated, and a display start condition that a magnitude of the inclination of the radiation detector is within a reference range.

20. A non-transitory computer readable recording medium storing a program causing a computer to perform the radiation imaging method according to claim 19.

* * * * *